United States Patent [19]
Fabrizio

[11] Patent Number: 5,657,514
[45] Date of Patent: Aug. 19, 1997

[54] ANGLE FIT BELT CLIP

[75] Inventor: Robert A. Fabrizio, Norwalk, Conn.

[73] Assignee: Acumen, Inc., Sterling, Va.

[21] Appl. No.: 577,015

[22] Filed: Dec. 22, 1995

[51] Int. Cl.$^6$ .................. A44B 11/00; A61B 5/00
[52] U.S. Cl. .................. 24/265 BC; 24/200; 24/265 R; 128/696
[58] Field of Search .................. 24/265 BC, 265 C, 24/265 R, 265 AL, 300, 301, 302, 482, 163 K, 179, 200

[56] References Cited

U.S. PATENT DOCUMENTS

| | | | |
|---|---|---|---|
| 245,761 | 8/1881 | Anderson | 24/200 |
| 311,691 | 2/1885 | Thompson | 24/200 |
| 825,395 | 7/1906 | Kennelly et al. | 24/197 |
| 1,452,854 | 4/1923 | Taylor et al. | 24/200 |
| 1,541,701 | 6/1925 | Gaunt | 24/200 |
| 3,279,012 | 10/1966 | Gold | 24/200 |
| 4,470,176 | 9/1984 | Vermeulen et al. | 24/265 AL |
| 5,105,511 | 4/1992 | Shahin et al. | 24/200 |
| 5,333,768 | 8/1994 | Krentz | 224/215 |
| 5,361,953 | 11/1994 | Nichols | 24/200 |
| 5,464,021 | 11/1995 | Birnbaum | 128/696 |

FOREIGN PATENT DOCUMENTS 0357953  9/1922  Germany .................. 24/200

*Primary Examiner*—Victor N. Sakran
*Attorney, Agent, or Firm*—Evenson, McKeown, Edwards & Lenahan, P.L.L.C.

[57] ABSTRACT

An angled belt clip for diverse worn articles such as heart rate monitors, swimsuits and the like prevents slippage of the article from the proper location on the wearer's body. The clip is provided with an upwardly or downwardly angled portion which holds an elastic strap or the like at a different height or location on the wearer's body than the height or location of the article. Alternatively, the article can be provided with an angled portion.

10 Claims, 4 Drawing Sheets

ANGLE FIT BELT CLIP

BACKGROUND AND SUMMARY OF THE INVENTION

The present invention relates to a belt clip and, more particularly, to an angled belt clip used for items included, but not limited to, wireless heart monitors, strapless bras, dresses, pants, skirts, backpacks, safety straps for climbing poles, women's sports tops, swimsuits and the like, where slippage of the item on a portion of the wearer's body presents a problem of appearance or functionality.

For example, wireless heart monitors are currently being made which use a transmitter belt worn on a person's chest below pectoral muscles and at heart level. I have found, however, that a person wearing such a monitor, when engaged in strenuous physical activity, encounters slippage of the monitor belt down the chest. This slippage prevents the heart rate monitor from working appropriately.

An object of the present invention is to provide a simple, yet effective solution to the problem of items slipping down the chest or other body portions where the items are held by a belt or elastic material but the belt is too loose where the elastic material begins to wear out.

The foregoing object has been achieved in accordance with the present invention by providing a belt clip which has a portion extending at an angle which allows the belt to bite into the contours of the body and prevent slippage.

According to one embodiment of the present invention, the angled portion of the belt clip can be arranged at about 20° degrees to the horizontal, although it will be understood that other angular relationships can be employed depending upon the intended results and the particular item being carried by the belt.

BRIEF DESCRIPTION OF THE DRAWINGS

These and other objects, features and advantages of the present invention will become more readily apparent from the following detailed description thereof when taken in conjunction with the accompanying drawings wherein.

DETAILED DESCRIPTION OF THE DRAWINGS

Figure 2:
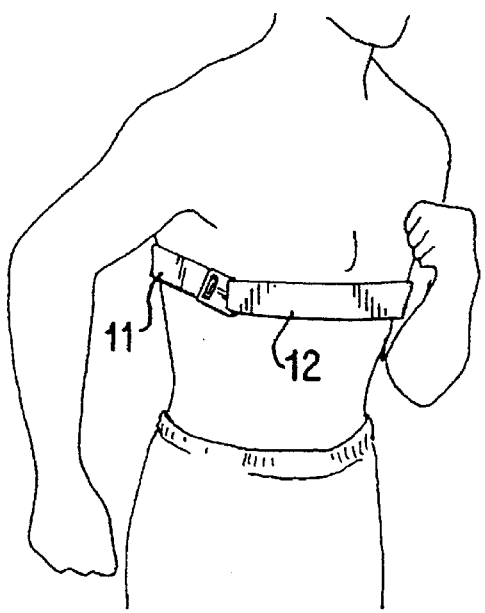
FIG. 2 is a partial view of the front of a person wearing the heart rate monitor chest belt shown in FIG. 1.
Figure 3:
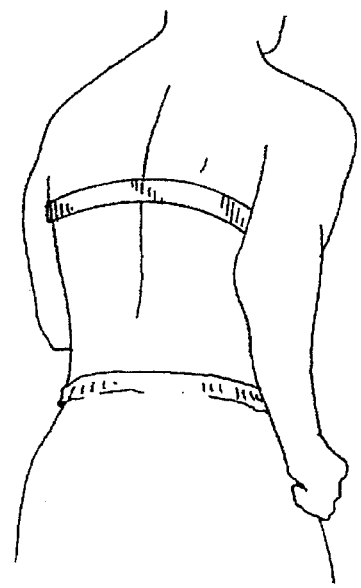
FIG. 3 is a partial rear view of the person shown in FIG. 2.
Figure 4:
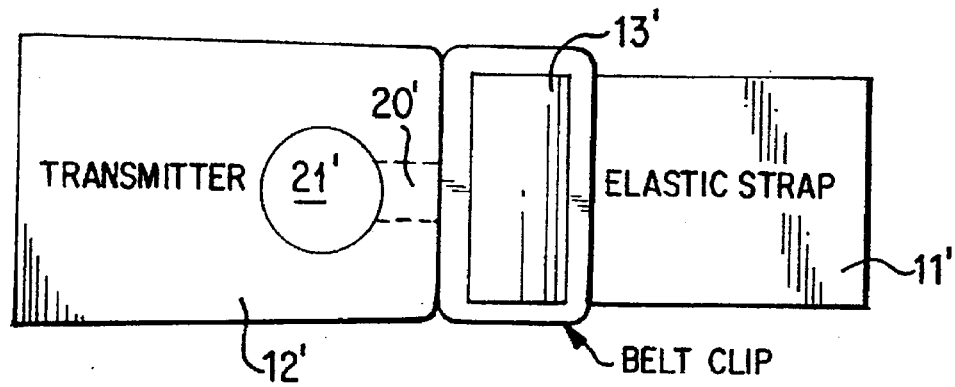
FIG. 4 is a view of a conventional belt clip for the heart rate monitor chest belt of FIG. 1.

Referring first to FIG. 4 which shows a conventional clip, an elastic strap 11' is removably detached from a heart rate monitor transmitter 12' through a belt clip 13'. In this conventional arrangement, the elastic strap 11', the transmitter 12' and the belt clip 13' are all arranged substantially in line so as to form a circle in one plane around the wearer's body, for example, around the chest just below the pectoral muscles as shown in FIG. 2. The free ends of the elastic strap 11' are provided with an extension 20' to which is integrally formed a button 21'. The extension 20' and button 21' are fitted with a mating recess and aperture on the transmitter 12' to constitute a secure but removable connection. Such a connection is generally known, and other suitable ways of connecting the strap to the article can also be used without departing from the scope of the present invention. As noted above, this type of arrangement has been found to slip down the chest, especially when worn by women, children or swimmers, particularly when the torso is V-shaped or very narrow or on any person when wearing a loose belt or when the elastic material begins to loose its elasticity.

Figure 1:
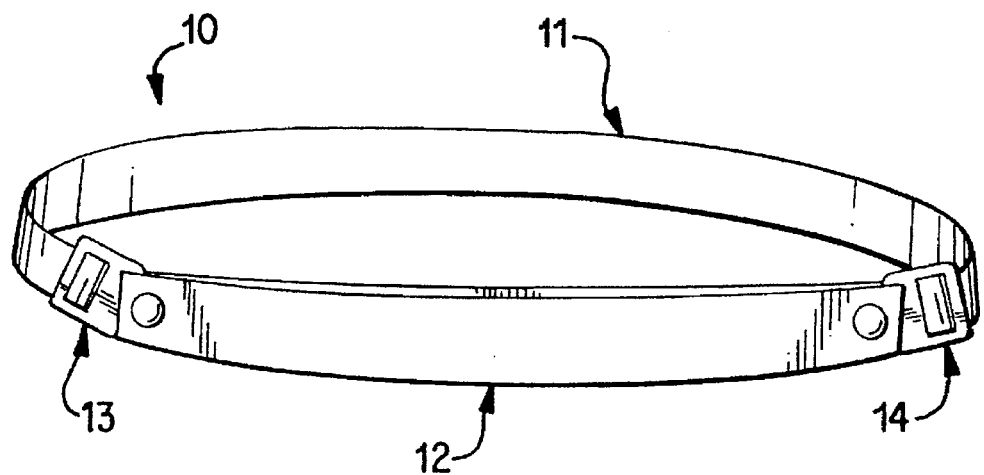
FIG. 1 is a perspective view of the heart rate monitor chest belt which uses an elastic strap and the angle-fit belt clip in accordance with the present invention.

I have found that this problem can be overcome by angling the belt or connecting clips such that the elastic strap 11 (FIG. 1) will travel around the back of the person in a different plane from the transmitter 12. That is, the elastic support strap 11 can be at a higher or lower level than the front transmitter 12 and possibly even on a slight curve. Such an arrangement allows the elastic strap to bite into the contour of the person's body without any discomfort. In fact, this arrangement provides a more stable and comfortable support to maintain the belt at the desired position and more closely follow the natural contour of the body. This is particularly important in the case of heart rate monitors where the location of the device is important for the proper functioning of the monitor.

Figure 5A:
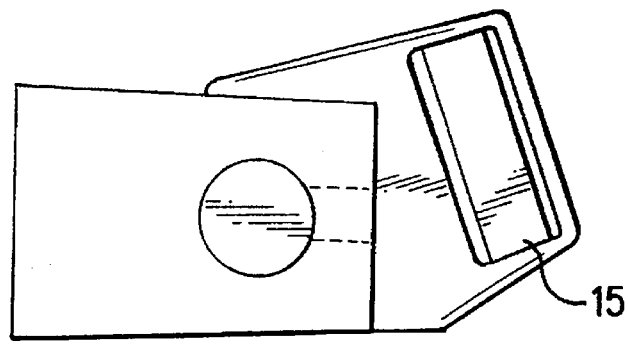
FIGS. 5a through 5h are different embodiments of an angle-fit belt clip used in the chest belt of FIG. 1.
Figure 5B:
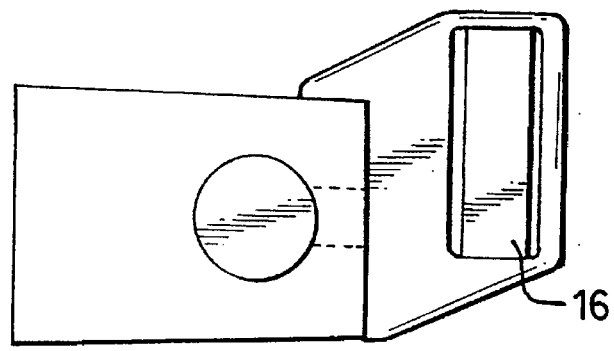
Figure 5C:
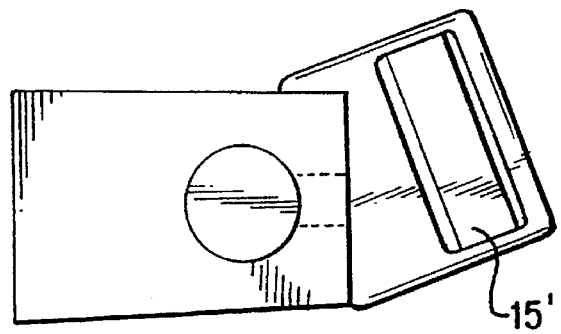

FIGS. 5a through 5h show different configurations of the belt clip. For instance, FIGS. 5a through 5c describe an arrangement in which the elastic strap will be at a higher level than the front portion. In FIG. 5a, the elastic strap will be secured around an angled post 15, as is also the case in FIG. 5c such that the elastic strap will be on a plane which intersects the plane in which the transmitter is located, whereas in FIG. 5b the elastic strap will be secured around a vertically disposed post 16.

Figure 5D:
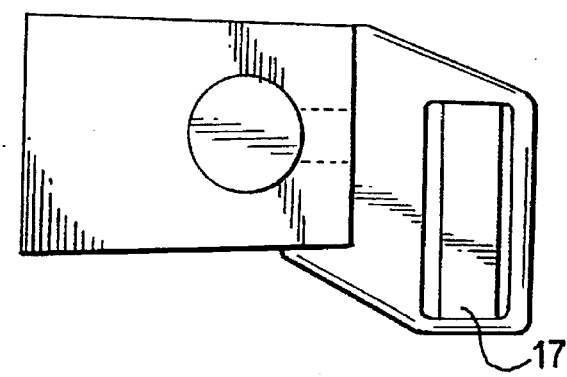
Figure 5E:
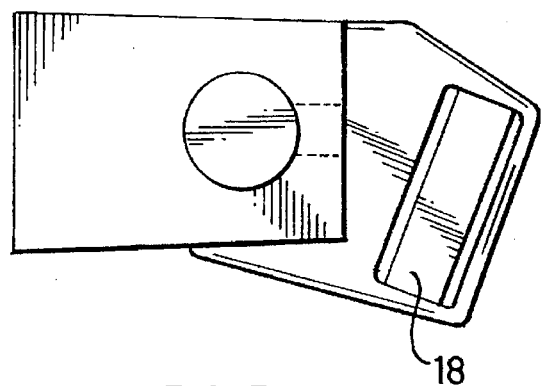
Figure 5F:
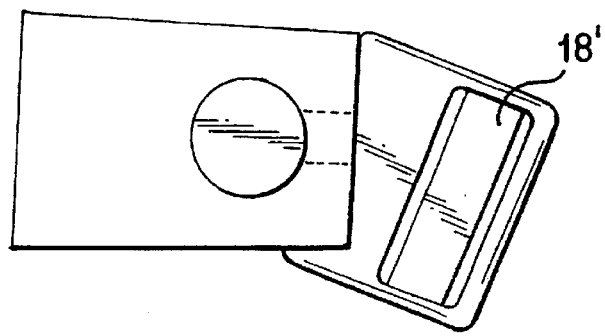

In FIGS. 5d through 5f, the elastic will be secured at a lower level than the front portion. Again, the elastic support will be secured either at a vertically disposed post 17 (FIG. 5d) or an angled post 18 (FIGS. 5e and 5f).

Figure 5G:
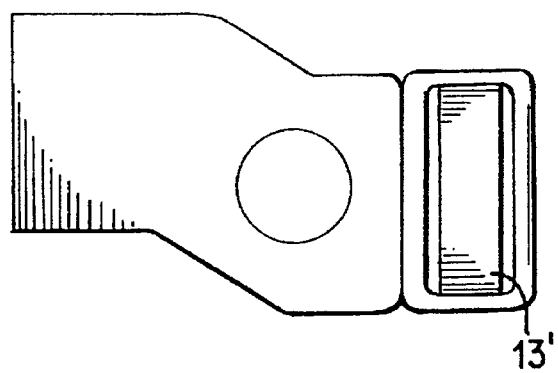
Figure 5H:
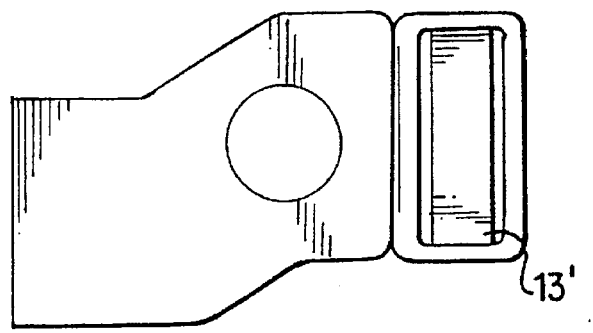

In the embodiments of FIGS. 5g and 5h, the belt clip corresponds essentially to the conventional design shown in FIG. 4, but the front portion is angled through a transition portion either above (FIG. 5g) or below (FIG. 5h) the belt clip 13' to achieve substantially the same result as in the embodiments of FIGS. 5a through 5f.

The angled portion can be approximately 20°, but it is to be understood that other angles can be utilized depending upon the item being worn and the purpose for which it is used. For example, the angle used in the illustrated wireless heart rate monitor with a transmitter belt worn on the chest just below the pectoral muscles may well be different from the types of angles used for strapless bras or backpacks. An essential feature, however, is that the front and back portions be arranged in different planes on the body and possibly with a curve.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. An arrangement for maintaining items at a desired position on a person's chest, comprising:
   a first portion having spaced ends extending on one side of the person's chest,
   a separate second portion having spaced ends extending on another side of the person's chest, and
   a pair of belt clips, each of the belt clips being provided between the first and second portions and having an angular displacement for positioning the first and second portions at different height positions on the person's chest and non-rotatably connecting each of the spaced ends of the first and second portions for maintaining the first portion and the second portion at the different height positions on each side of the person's chest to prevent slippage of said items.

2. The arrangement according to claim 1, wherein the each belt clip has an angled portion connected with one of the first portion and the second portion.

3. The arrangement according to claim 2, wherein the first and second portions, at least in the vicinity of the belt clip are arranged to extend in parallel planes.

4. The arrangement according to claim 2, wherein the first and second portions, at least in the vicinity of the belt clip are arranged in intersecting planes.

5. A belt clip for use with an article worn on a chest of a living being, comprising a portion which is angled to an imaginary horizontal plane to provide an angular and non-rotatable displacement between a first strap carrying the article at a first defined height position on the chest and a second strap at a second defined height position at a back portion of the living being, with the first and second height positions being different from each other to prevent the slippage of said article.

6. The belt clip according to claim 5, wherein the first and second straps, at least in an adjoining vicinity thereof, extend in parallel planes.

7. The belt clip according to claim 5, wherein the first and second straps, at least in an adjoining vicinity thereof, extend in intersecting planes.

8. A method of using a pair of belt clips to maintain at least one article at a desired position on a person's chest, comprising the steps of arranging a first portion of the article such that spaced ends of the first portion are on each side of the person's chest, arranging a separate second portion of the article on a back portion opposite the person's chest such that spaced ends of the second portion are adjacent the spaced ends of the first portion, and arranging the belt clips such that an angled portion thereon non-rotatably connects the spaced ends of the first and second portions and provides an angular displacement between the first and second portions to maintain the portions on different positions on the chest without slippage caused by physical exertion.

9. The method according to claim 8, wherein the first and second portions, at least in the vicinity of the belt clips, extend in parallel planes.

10. The method according to claim 8, wherein the first and second portions, at least in the vicinity of the belt clips, extend in intersecting planes.

* * * * *